(12) United States Patent
Tucker et al.

(10) Patent No.: US 9,373,177 B2
(45) Date of Patent: Jun. 21, 2016

(54) DETERMINATION OF AN OPTIMUM COLOUR COMBINATION OF AN IMAGE ON A BACKGROUND BY MEASUREMENT OF RESPONSE TIME OF A SUBJECT VIEWER

(75) Inventors: Marlon Tucker, Winchester (GB); Nigel Philip Evelyn-Dupree, New Milton (GB)

(73) Assignee: Biometrics Screening Limited, Buckinghamshire (GB)

( * ) Notice: Subject to any disclaimer, the term of this patent is extended or adjusted under 35 U.S.C. 154(b) by 281 days.

(21) Appl. No.: 14/003,144

(22) PCT Filed: Mar. 5, 2012

(86) PCT No.: PCT/GB2012/000219
§ 371 (c)(1),
(2), (4) Date: Sep. 24, 2013

(87) PCT Pub. No.: WO2012/120256
PCT Pub. Date: Sep. 13, 2012

(65) Prior Publication Data
US 2014/0009489 A1      Jan. 9, 2014

(30) Foreign Application Priority Data

Mar. 4, 2011   (GB) .................................. 1103705.8

(51) Int. Cl.
G09G 5/02        (2006.01)
G06T 11/00       (2006.01)
A61B 3/032       (2006.01)
A61B 3/06        (2006.01)
A61B 5/16        (2006.01)

(52) U.S. Cl.
CPC ............... *G06T 11/001* (2013.01); *A61B 3/032* (2013.01); *A61B 3/066* (2013.01); *A61B 5/162* (2013.01)

(58) Field of Classification Search
None
See application file for complete search history.

(56) References Cited

U.S. PATENT DOCUMENTS

| | | | | |
|---|---|---|---|---|
| 6,729,729 B1* | 5/2004 | Irons | | 351/242 |
| 2011/0027766 A1* | 2/2011 | Yoo et al. | | 434/262 |
| 2011/0249026 A1* | 10/2011 | Singh | | 345/630 |
| 2011/0270123 A1* | 11/2011 | Reiner | | 600/558 |

* cited by examiner

*Primary Examiner* — Edward Martello
(74) *Attorney, Agent, or Firm* — William H. Bollman

(57) ABSTRACT

Recently there has been an increase in awareness of work/life stressors and their debilitating affect on human functionality. These stressors can arise from environmental conditions, poor quality artificial lighting and/or too much or too little ambient lighting, poorly configured or ineffectual display screens. The invention includes a method of presenting an image to be viewed by the subject on a background of a first color, and by way of an iterative process a user is led through a series of screens in order to determine their optimum color combination. A means is provided for storing reaction times and for varying the image to be viewed in a second and subsequent interval, so as to derive second and subsequent reaction times. An optimum color is selected that corresponds to the quickest reaction time.

17 Claims, 16 Drawing Sheets

| # | R | G | B |
|---|---|---|---|
| 1 | 255 | 255 | 255 |
| 2 | 255 | 255 | 150 |
| 3 | 255 | 255 | 100 |
| 4 | 255 | 255 | 50 |
| 5 | 255 | 255 | 0 |
| 6 | 255 | 150 | 255 |
| 7 | 255 | 100 | 255 |
| 8 | 255 | 50 | 255 |
| 9 | 255 | 0 | 255 |
| 10 | 150 | 255 | 255 |

FIG. 3a

| # | REACTION TIME/SECONDS |
|---|---|
| 1 | 5.2 |
| 2 | 6.4 |
| 3 | 6.6 |
| 4 | 7.0 |
| 5 | 7.5 |
| 6 | 4.9 |
| 7 | 6.0 |
| 8 | 6.4 |
| 9 | 6.8 |
| 10 | 6.6 |

FIG. 3b

|    | R   | G   | B   |
|----|-----|-----|-----|
| 11 | 255 | 130 | 255 |
| 12 | 255 | 140 | 255 |
| 13 | 255 | 150 | 255 |
| 14 | 255 | 160 | 255 |
| 15 | 150 | 170 | 255 |
| 16 | 100 | 140 | 255 |
| 17 | 50  | 140 | 255 |
| 18 | 255 | 140 | 150 |
| 19 | 255 | 140 | 100 |
| 20 | 255 | 140 | 50  |

FIG. 4a

| # | REACTION TIME/SECONDS |
|---|---|
| 11 | 5.9 |
| 12 | 5.5 |
| 13 | 4.9 |
| 14 | 4.2 |
| 15 | 3.7 |
| 16 | 5.0 |
| 17 | 5.8 |
| 18 | 6.3 |
| 19 | 7.2 |
| 20 | 7.8 |

FIG. 4b

| Name | Hue | Original value | 1 step lighter | 2 steps lighter | 3 steps lighter |
|---|---|---|---|---|---|
| snow4 | 0° | #8B8989 | #ADACAC | #D0CFCF | #F2F2F2 |
| snow3 | 0° | #CDC9C9 | #DAD7D7 | #E6E4E4 | #F3F2F2 |
| snow2 | 0° | #EEE9E9 | #F0ECEC | #F2EEEE | #F4F1F1 |
| rosybrown4 | 0° | #8B6969 | #AF9595 | #D2C3C3 | #F4F0F0 |
| dustyrose | 0° | #856363 | #AC9090 | #D0C0C0 | #F4F0F0 |
| salmon5 | 0° | #6F4242 | #A96E6E | #CFAFAF | #F5EFEF |
| rosybrown | 0° | #BC8F8F | #CFAFAF | #E2CFCF | #F5EFEF |
| rosybrown3 | 0° | #CD9B9B | #DBB7B7 | #E9D2D2 | #F7EEEE |
| indianred4 | 0° | #8B3A3A | #BF6666 | #DBA9A9 | #F7EDED |
| sgisalmon | 0° | #C67171 | #D79A9A | #E7C4C4 | #F8EDED |
| brown | 0° | #802A2A | #C54E4E | #DF9D9D | #F9ECEC |
| indianred | 0° | #CD5C5C | #DC8C8C | #EABCBC | #F9EBEB |
| indianred3 | 0° | #CD5555 | #DC8787 | #EAB9B9 | #F9EBEB |
| brown | 0° | #A52A2A | #D45757 | #E7A1A1 | #FAEBEB |
| brown4 | 0° | #8B2323 | #D04545 | #E59898 | #FAEBEB |
| firebrick5 | 0° | #8E2323 | #D14646 | #E69898 | #FAEBEB |
| brown | 0° | #A62A2A | #D55858 | #E7A1A1 | #FAEBEB |
| orange | 0° | #CC3232 | | | |

(Extracted from http://www.december.com/html/spec/colorshades.html)

FIG. 8a massa proin hendrerit sit ornare erat in dolor proin cubilia nisl diam ante sodales sectetuer ante elementum neque tellus tincidunt in pede morbi vel varius imperdiet dictum

FIG. 8b

DETERMINATION OF AN OPTIMUM COLOUR COMBINATION OF AN IMAGE ON A BACKGROUND BY MEASUREMENT OF RESPONSE TIME OF A SUBJECT VIEWER

FIELD OF THE INVENTION

The present invention relates to an apparatus for, and a method of, determining and measuring fatigue using colour combinations. More particularly, but not exclusively, the invention relates to an apparatus for, and a method of, determining, in an objective manner, an optimum colour combination of a background colour of display (or screen) and images that are displayed or projected thereon, for use as part of a vision enhancement system and so as to reduce screen fatigue and improve a user experience.

BACKGROUND OF THE INVENTION

Recently there has been an increase in awareness of work/life fatigue and its debilitating effect on human functionality. It is an accepted fact that increased stress affects mood, performance at work and interpersonal relationships. As more and more people spend a greater amount of their active time (work and leisure) in front of a display, it is becoming increasingly important to enhance the experience.

As an ever increasing number of workers are office based, there is an increasing amount of reported cases of work related stress. Sources of stress often lead to fatigue at the workplace include: environmental conditions, such as poor quality artificial lighting and/or too much or too little ambient lighting; poorly designed displays or (incorrect) and ineffectual visual aids that permit unfettered access to digital data presented on display screens.

In a paper published in "Journal of Behavioural Optometry"; Vol. 7, 1996 Number 5, entitled "Stress and Eye: New Speculations on Refractive Error" by Merrill D. Bowan, there is a discussion and explanation as to a theory of ametropias and that refractive errors are outcomes of resulting physiological strains.

The author proposes a General Adaptation Syndrome (GAS) as a stress adaptive response. It is postulated that visual coping mechanisms are challenged by a variety of conditions so as to produce homeostatic responses that alter scleral and crystalline lens dynamics, leading to posterior chamber distention and hyperopization.

The author measures these as adaptive diseases: myopia, hyperopia and astigmia and attributes their existence as a precursor of adaptation exhaustion exacerbated by stress. It is argued that for the vision specialist, the existence of refractive errors is a cause of physical stress and vice versa.

These are the sorts of stress that are often suffered by employees who spend a large proportion of their working day in front of visual display units (VDUs), screens or other displays. These stresses are often present in the chain of causation leading to posterior chamber distention and hyperopization and which subsequently can give rise to, or exacerbate, fatigue related visual disruption presenting and/or manifesting in coping strategies like monocularity, unstable or unsustainable vergence, double vision and even eye turns. This visual disruption can in turn give rise to fatigue related inability to maintain a good posture, which in turn can increase the risk of repetitive stress injury (RSI), temporary harm or longer lasting injury including muscular skeletal disorders, which can ultimately lead to temporary or permanent disability.

To date there has not been a reliable objective method of assessing risk of over exposure to such displays, regardless of compliance with current health and safety legislation (in many countries including the UK) that recognises that fatigue may also be an overarching potential causation in repetitive strain injury (RSI) type injuries. Such other injuries include a variety of other stress related diseases, such as muscular skeletal disorders (MSDs) as reported by the UK Health and Safety Executive (HSE) in a Report entitled "Better Display Screens" (RR561 in 2007) which referred to aspects of display systems and monitors.

It has been noted, with the proposed introduction, in April 2012 of a revised EU Directive (Directive 90/270/EEC—Display Screen Equipment) on 'Manual Handling and Display Screen Equipment (DSE), that employers are resisting being placed under increased legislative pressure to ensure that reasonable steps are being taken to prevent and/or mitigate stressors known to be a common risk that debilitates operator performance.

Risk assessments are legally required by various Health and Safety regulators in many jurisdictions. A risk assessment should fully assess all aspects of an employees' workplace, their equipment/tools and normal working conditions. Risk assessments should also be carried out at regular periods, or on demand or when there is a change in equipment, work conditions, environment or equipment operators.

Users or operators who interact with visual display units (VDUs) or Display Screen Equipment (DSE) for even relatively short periods of time, may be susceptible to, and/or at increased risk of, acquiring harmful visual coping strategies characterised by computer vision syndrome (CVS).

CVS is a condition associated with a range or collection of harmful symptoms indicative of the visual systems physiological and/or neurological response to being under strain. Such physiological and/or neurological strain gives rise to what is often referred to as "screen fatigue" associated with a mild form of 'cyber sickness' that has been noted to be exacerbated by certain, virtual 3-D technologies being introduced across media, including: micro screen, hand held equipment and mobile devices, as well as static display screen equipment that, following research, now carries a warning that children are particularly susceptible and may suffer long term damage to their visual systems. This is another form of "visual stress" resulting in systemic fatigue.

Visual stress can also trigger the onset of eye ache and tension headaches. If such eye ache and headaches are experienced regularly they can give rise to, or even promote, increased (emotional) psycho-physiological stress, which can manifest itself as performance anxiety. These are often the result of a range of coping strategies, for example when subjected to prolonged use of display screen equipment (DSE) in addition to increased.

The eyes and visual system can therefore be considered to be connected to an organism physically, chemically and emotionally. Therefore, their function or dysfunction is inextricably linked to the well-being of the individual.

This stress related fatigue, if it remains unmitigated, can in turn lead to problems with employee well-being, attendance and/or increased reporting of errors, irascible behaviours, absenteeism and time off as sick. There is also evidence that these effects may be associated with lower employee self esteem, poor morale and an increase in risk of harm through other hazards linked to the workplace resulting in higher staff turnover.

There is therefore an ever-greater need for an apparatus and a related method for determining and measuring fatigue, especially operator fatigue.

PRIOR ART

International Patent Application WO-A-2007/132173 (Dupree) discloses an apparatus for determining risk assessment. The apparatus involves obtaining a characteristic measurement of an eye; deriving data from that measurement; and processing the data to derive a value indicative of a state and/or function and/or operational condition of the eye at a given instant; and transferring data to an output for assessment.

Various guidelines and 'best practice' procedures exist. However, one of the problems encountered with measuring visual strain is to work out the amount of synchronicity between motor function of the eyes and the physiological/psychological effect that this may have.

There are a number of challenges that are posed by stereo (binocular) vision. One of these is image stabilisation for example when viewing a moving object and the need to achieve uniform registration of the object by stereoscopic imaging (left and right eyes).

Another practical problem that is encountered in binocular visual systems is that of interlacing separate images from two eyes, which typically have non-identical focussing capabilities and different colour perception. Added to this is the need to achieve stable convergence in support of depth perception, which is not always effected with the same efficacy by each eye.

Other problems that are encountered when there is relative motion between the viewer and objects being viewed, for example, if the viewer is in a moving vehicle. When this occurs there is a need for image stabilisation.

Prolonged exposure to VDUs or displays, and the increasing uptake of liquid crystal displays (LCDs) over cathode ray tubes (CRTs), also poses an additional strain of high frequency flicker and/or interference effects, where other sources of artificial light or adjacent screens can give rise to effects similar to strobing.

As a consequence of the above, and the increased contact with screens and workstations, it is not surprising that human visual systems, especially of office based workers, are subject to a mass of stressors for which historically they have not evolved.

Reference is also made to published International Patent Application Number WO-A1-2004/112598 (Tintavision) which describes a method of testing applicable to the provision of a vision aid, such as the selection of a tint for a VDU screen, to assist in alleviation of symptoms in dyslexia and other optical disorders. The method employs a quantitative approach to the identification of the colorimetric parameter within three dimensions of colour space applicable to the vision aid for optimal patient visual performance. A test procedure, in which eye trace parameters are associated with a given value of each of the three colorimetric parameters of the vision aid, are used to select the optimum colorimetric values of the vision aid.

The arrangement is complex and requires supervision for its use and the interpretation of the data.

Russian Patent Application RU-A-2077254 (Moscow Eye Disease Research Institute) describes an investigation technique for determining colour sensitivity and which uses sensing techniques to monitor the reaction of an eye at an instant when brightness stimuli are of equal intensity across a field of view.

Whilst proposing solutions to similar problems, none of the aforementioned publications describes or suggests a system for self-assessment interactively determining occupational or otherwise risk of screen fatigue and measuring sub-optimal/optimum propinquity for screen interface characteristics for use unsupervised and by which fatigue may be mitigated using contrast colour combinations.

A problem has therefore been that there was no dedicated equipment or methodology to perform an objective measurement of stress, that is based on a subject's performance at a particular instant, rather than on a subjective measurement, which is obtained from the individual or in an optician's or optometrist's refractive tests when prescribing personal protective equipment (PPE).

In a paper entitled "Visual Reaction Time Measurements with Background Provided by Colour Monitors", by Jimenez del Barco et al, published in Journal of Optics (Paris) 1991, vol 22, number 3 at pages 129-133, a study related visual reaction time (VRT) for an achromatic stimulus on a cathode ray tube (CRT) monitor.

The paper by del Barco et al revealed a relationship between the VRT and the chromaticity of an adaptive background as a function of the distance of the stimulus from a parafoveal zone which a colour sensitive region of the retina of the eye.

A theory, proposed by Richard Solomon known as the colour opponent process, is a colour theory that states that the human visual system interprets information about colour by processing signals from cones and rods in an antagonistic manner. The three types of cones (L for long, M for medium and S for short) have some overlap in wavelengths of light to which they respond, so it is more efficient for the visual system to record differences between the responses of cones, rather than each type of cone's individual response.

The opponent colour theory suggests that there are three opponent channels: red-versus-green, blue-versus-yellow, and black-versus-white (the latter type is achromatic and detects light-dark variation or luminance). Responses to one colour of an opponent channel are antagonistic to those to the other colour. That is, opposite opponent colours are never perceived together—there is no "greenish red" or "yellowish blue".

Trichromatic theory defines the way the retina allows the visual system to detect colour with three types of cones. An alternative opponent process theory accounts for mechanisms that receive and process information from cones. Though the trichromatic and opponent processes theories were initially thought to be at odds, it later came to be understood that the mechanisms responsible for the opponent process receive signals from the three types of cones and process them at a more complex level.

U.S. Pat. No. 6,729,729 (Tintavsion) describes a method of reducing eye strain and symptoms associated with dyslexic readers and differentiates between so-called array optical functions, (such as reading), and non-array optical functions, (such as scanning for a word or image in large mass of text and/or images). A solution is proposed in which a set of results is interpreted by a skilled reviewer and a modified colour screen is proposed.

The technique aims to reduce eyestrain for dyslexic readers and does not propose a method of determining or measuring or overcoming fatigue using colour combinations. Furthermore the precedence of a trained optometrist or optician is required in order to interpret the results.

Despite the foregoing there is still a need for equipment and/or methodology for performing an objective measurement of stress that is based on a subject's performance and ideally a stress that determines and measures fatigue using colour combinations.

An object of the invention is therefore to provide an improved system and method of determining and measuring fatigue using colour combinations, which does not entail the presence of a skilled optometrist or clinician and one which can be readily be performed by a user in order to enhance a user experience with a screen or visual display.

Another object of the invention is to provide an improved system for determining stress levels without requiring any invasive method of detecting, measuring and assessing operator fatigue: that is without the need for sampling bodily fluids or extracting blood for chemical analysis.

A further object is to provide a method of determining stress levels without requiring any invasive method for detecting the symptoms associated with spectral lighting hazards, for example associated with alertness or fatigue by stimulating or suppressing the production of melatonin linked to Circadian rhythms in humans.

SUMMARY OF THE INVENTION

According to a first aspect of the present invention there is provided a method of determining an optimum colour combination of an image on a background that is different colour to the image, comprising the steps of: a) at a start time presenting a first colour combination of an image and background, to a subject; initiating a timer when the first colour combination is presented to the subject and stopping the timer when the subject has registered a stereoscopic image perceived by right and left eyes, so as to provide a first reaction time corresponding to the first colour combination; storing the first reaction time; and b) at the start of a second time interval initiating the timer when a second colour combination of an image and background, is presented to the subject and stopping the timer when the subject has registered the stereoscopic image, so as to provide a second reaction time corresponding to the second colour combination; storing the second reaction time; comparing the first and second reaction times, characterised in that a third colour combination, corresponding to the quickest reaction time, is selected in accordance with a colour chart; and the combination corresponding to the slowest reaction time is substituted with a third colour combination derived from the colour chart; and repeating steps a) and b) until an optimum colour combination for the subject is achieved.

Once times are obtained they are mapped onto a colour or chromance chart which provide colours and associated with each colour, three other colours based on the original colour but with higher or lower light values. These charts are used to define sensitivity to contrasting colour schemes.

Ideally a linear interpolation is performed between first and second points on the colour chart that correspond to the first and second reaction times. In an alternative arrangement, where for example the colour chart may be, for example, the colour chart or CIE 1960 UCS (MacAdam (u,v) chromaticity diagram CIE), of the type shown at http://en.wikipedia.org/wiki/File:CIE_1960_UCS.png. However, it is appreciated that colour charts may take a variety of forms and this one is only mentioned by way of an example.

An alternative technique may be used such as an extrapolation technique or one which employs polynomial interpolation or an extrapolation technique that uses or determines a third variable from one or more existing variables or alternative numerical techniques such as Runge-Kutta or Newton-Raphson techniques.

Alternative interpolation techniques may be used which employ historical data for example derived from a population of users.

An example of a typical colour chart that uses hexadecimal is shown at http://www.december.com/html/spec/color-shades.html. In this chart, the first column lists the name of the colour. The second column lists the colours hue in degrees of the colour circle with 0°=red; 120°=green; 240°=blue. The next two columns are hexadecimal red, green, and blue codes for the colour. The next three pairs of columns show swatches of colour based on the original value, but with decreasing or increasing light based on a step size. The step size of increasing light is intended to give three lighter swatches of the original value. The specific colours (swatches) that are depicted are calculated to be equidistant from an original light value to a light value of 95%.

By selecting a specific contrast colour combination that is based on two earlier combinations—using a colour or chromance chart—the method interactively and quickly homes in to an ideal colour combination for a user, automatically and without any supervision by trained practitioner or optometrists. An advantage is therefore that is can be delivered to a user's personal display equipment, computer, laptop or workstation and the user can be lead, by way of a set of easy-to-follow instructions, to optimise the interface between their display screen equipment and themselves.

The time taken for the left and/or right eyes to adjust or adapt when they can or cannot maintain or sustain a single or stereoscopic stable image is important because it provides an indication of the level of fatigue of a user. One preferred way in which this time is obtained is to provide a user with serial sequential task of disparate symbols to differentiate or for example a piece of meaningless text, which cannot be scanned (read fluently or at speed) because the text comprises a passage of made up words.

It has been found that such construction of task, or in this example case, the text symbols forces a user to focus on individual target or word like forms and not to quickly 'skim' them, so ensuring a subjects eye/eyes have correctly registered the word forms and so reducing the opportunity of a user to 'cheat 'by attempting to read and remember or solely scan subject matter presented on screen.

The invention, in a preferred embodiment therefore, provides a non-invasive method of detecting, measuring and assessing the conditional state and performance of an individual.

Ideally a calibration, or a benchmarking step, is performed as part of a risk assessment using a control background or screen colour that is the same before an assessment is made and after assessment has been made as a datum. The results of this are ideally stored in association with a user's identity, such as a username, and/or a date of birth and/or a password, as well as the date on which the benchmarking assessment was made.

Optionally in an alternative embodiment, a detector, which may be a camera, charge coupled device (CCD) array or other motion detector may be employed in order to provide a signal indicative of the state of an eye of a user. This signal in combination with other data, such as reaction times, can be combined so as to provide an alert signal or alarm, for example to an operator of a machine or vehicle, thereby alerting them to symptoms of fatigue.

Optionally a machine may be provided with an alarm or a disable signal, so as to render the machine inoperable or to drive the machine to a passive or safe state, thereby avoiding injury to an operator who may be showing signs of fatigue or tiredness.

According to another aspect of the present invention there is provided a display that is adapted to determine an optimum colour combination of an image on a background that is different colour to the image, comprising: a means for presenting a colour combination of an image and background to a subject; and a timer, which is adapted to initiate when a first colour combination is presented to the subject, so that, in use the subject records the time when a stereoscopic image is registered by right and left eyes, thereby providing a first reaction time corresponding to the first colour combination; a means for storing the first reaction time; and a switch for presenting a second colour combination of an image and background, at the start of a second time interval and initiating the timer, so that, in use the subject records the second time interval when the subject has registered the stereoscopic image, so as to provide a second reaction time corresponding to the second colour combination; storing the second reaction time; a means for comparing the first and second reaction times, characterised in that a means automatically selects a third colour combination, corresponding to the quickest reaction time, from a colour chart and in accordance with software; and the colour combination corresponding to the slowest reaction time is substituted with the third colour combination steps a) and b) until an optimum colour combination for the subject is achieved.

Ideally once the ideal colour combination has been provided a user has an option of associating that colour combination with his/her user identity and/or password, thereby ensuring that the optimum colour combination is provided to a user at a particular display or screen on demand.

The display may be used to detect, measure and assess levels of stress and/or fatigue.

Recalibration using a control background is ideally carried out using a white background. However, it is understood that the colour of the background may be any neutral colour and is optionally stored as a pre-set colour mix of signals from red, green and blue primary colour sources.

Thus by use of the invention, and the related apparatus, it is possible to ascertain the level of fatigue which an eye is experiencing.

A compensator can be added in order to accommodate variations in ambient light conditions that can be experienced with background fluctuations. Such fluctuations might be typically when viewing a display in a bright sunlit room or the same display when the room is darkened. The compensator may include a photosensitive device.

Ideally the method can be used to determine fatigue by assessing functional visual performance by selecting colours in subsequent intervals. One way in which this is achieved is by varying the colour of a display and background screen and this can be achieved by altering the hue or intensity of one or more colours of the image and the display.

The method ideally determines functional visual performance using colours of a display of an array of pixels, in subsequent time intervals and by varying the relative intensity of primary colours.

Advantageously colours are varied automatically. Alternatively a user machine interface (UMI) is provided and a user is able to perform the measurement under control of a menu or series of instructions.

Instructions may be prompted automatically, instructions may appear on a screen or they can be audible.

The arrangements is ideally adapted to provide interactivity so as to, for example, adjust preset increments, during the macroscopic tuning phase, fine tuning phase or both, so as to seek a best response.

Ideally the colour of the screen or display is varied by increasing or decreasing the intensity of a primary colour in preset increments, whilst maintaining other colours at a fixed brightness and this variation is in a first, macroscopic stage.

Advantageously second and subsequent stages of tuning, and fine tuning stages, are performed in an iterative manner, so as to derive a precise colour combination of background and image that a user is comfortable to use.

Images that may be used include: alphanumeric characters, symbols, patterns or any other sign or symbol that can be represented graphically. These symbols or patterns may be animated so that they move around a screen or display. There may be one or more image. Other images may be used for younger people or people who cannot read, such as recognisable or well-known images or animals or cartoon characters.

Advantageously images are presented in the form of text for a reader to read or scan as this tends to be a reliable technique of ensuring the eyes fixes fixate and saccade smoothly between a target image and register the two images.

A headset with goggles or other non-contact monitoring system may be used in order to track and/or monitor eye movements and provide data indicative of the precise movements of eyes and their tracking paths that can identify the level of visual decremation under strain or stress induced by presentation of images that may be encountered when using display screen equipment (DSE).

Alternatively no additional equipment is needed other than a user-machine-interface (UMI) and a display screen operating in accordance with software.

Provision for edge detection of images may be included in the apparatus and this is typically achieved by monitoring and tracking eye movement as eyes follow moving images to be viewed. Ideally this is achieved under control of software to maintain reproduction of test conditions, Preferably a means is provided to vary one or more primary colours automatically and in accordance with an algorithm as defined in software. This may be achieved by a manual control but is ideally performed by an automatic controller which may optionally be supervised by a remote operator.

Preferably a user-machine-interface (UMI) is used to enable a user to assess his/her own visual fatigue and a score or percentage indicator is provided that corresponds to a particular screen. Optionally a datum is accessible before and/or after an assessment, so that an objective comparison may be made. Typically results or scores are stored and may be accessed for random or routine comparison.

Optionally remote access to a central computer with a micro-processor is provided by way of a connection to the Internet. Such an arrangement permits a third party to monitor individual measurement and maintain a record of long-term change of an individual's performance and optimum display screen calibration. A database may be provided for overseeing and managing this task.

Ideally the when configured the display apparatus is adapted to take into account motion detection and edge detection by the eye. This can be achieved, for example, by providing one or more images that move around a screen in a predictable or reproducible manner or in an entirely random manner. Likewise a piece of text may include words whose order can be shifted in a random manner, so as to reduce the opportunity of someone memorising a passage of text and therefore providing an artificially low time. The text may include meaningless words that include vowels and consonants so as to inhibit scanning or high-speed reading, thereby forcing a reader to focus on individual words.

An example of such a piece of text is, which is readable, but meaningless:

"massa proin hendrerit sit ornare erat in dolor proin cubilia nisi diam ante sodales sectetuer ante elementum neque tellus tincidunt in pede morbi vel varius imperdiet dictum"

According to another aspect of the invention there is provided a method of determining visual fatigue comprising the steps of: presenting a colour combination of an image on a background that is different colour to the image on a display to a user whereby at a start time a first colour combination of an image and background, is presented to a subject; initiating a timer when the first colour combination is presented to the subject and stopping the timer when the subject has registered a stereoscopic image perceived by right and left eyes, so as to provide a first reaction time corresponding to the first colour combination; storing the first reaction time; and b) at the start of a second time interval initiating the timer when a second colour combination of an image and background, is presented to the subject on the display and stopping the timer when the subject has registered the stereoscopic image, so as to provide a second reaction time corresponding to the second colour combination; storing the second reaction time; comparing the first and second reaction times, characterised in that a third colour combination corresponding to the quickest reaction time is selected in accordance with a colour chart; and the combination corresponding to the slowest reaction time is substituted with a third colour combination derived from the colour chart; and steps a) and b) are repeated until an optimum colour combination for the subject is achieved.

It is appreciated that other aspects of the method mentioned above, may be incorporated into the display apparatus. Likewise it is understood that dedicated on-board software is provided, which may be embedded as read only memory (ROM) or as electrically programmable read only memory (EPROM) or as a field programmable gate array (FPGA).

The invention is suitable for use with liquid crystal displays (LCDs) as well as with plasma screens and images projected from a projector onto a display or surface.

The invention will now be described, by way of examples only, and with reference to the accompanying drawings, in which:

BRIEF DESCRIPTION OF THE DRAWINGS

FIG. 3a is a table showing results for user attempts (1 to 10), and corresponding signals of colour intensities, for a first image and background colour combination;

FIG. 3b is a table corresponding to the attempts in FIG. 3a and shows reaction times;

FIG. 4a is a table showing results of user attempts (11 to 20), for a second image and background colour combination;

FIG. 4b is a table corresponding to FIG. 3a and shows corresponding reaction times;

FIG. 8a is an extract from a hexadecimal table, for example as shown at http://www.december.com/html/spec/color-shades.html;

FIG. 8b is an example of a passage of text which can be presented to a user.

DETAILED DESCRIPTION OF THE ILLUSTRATED EMBODIMENT

Figure 1A:
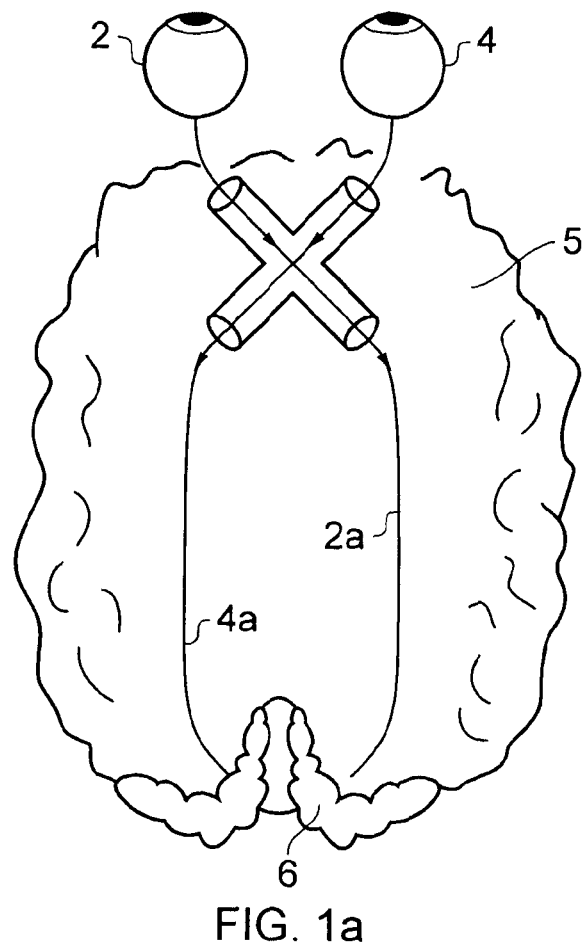
FIG. 1a is an overall diagrammatical view of human brain, showing the location of the eyes and the occipital region, illustrating the principle of stereoscopic vision and depicting diagrammatically visual performance.
Figure 1B:
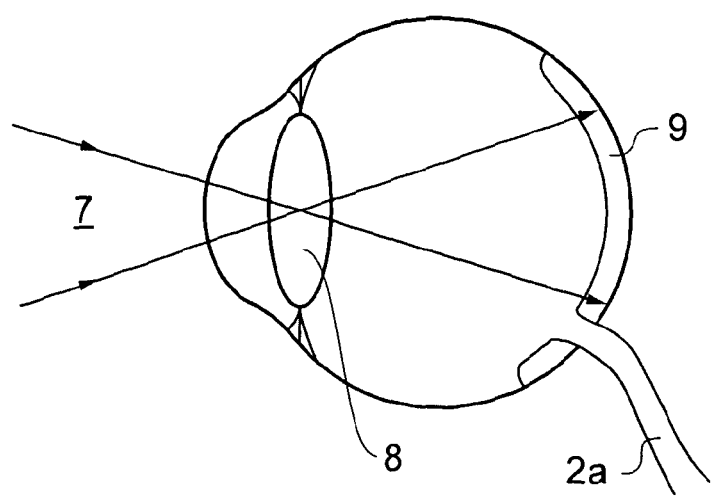
FIG. 1b is a diagrammatical section of a human eyeball.

Referring to the Figures generally and specifically to FIGS. 1a and 1b, there is depicted a human visual system comprising a pair of left 2 and right 4 eyes, each having an optic nerve 2a and 4a respectively that connects signals generated in them to a part of the brain 5 known as the occipital region 6 which is where image signals are interpreted. Image signals are obtained by the eyes 2 and 4, from light rays 7 emanating from a remote object (not shown) and are focussed by way of a lens 8 on to a retina 9.

Light is processed by the human visual system by cones and rods in an antagonistic manner. There are three types of cones (L for long wavelength light, M for medium wavelength light and S for short wavelength light) and these have some overlap in wavelengths of light to which they respond. It is therefore more efficient for the visual system to record differences between the responses of cones, rather than each type of cone's individual response.

Figure 2:
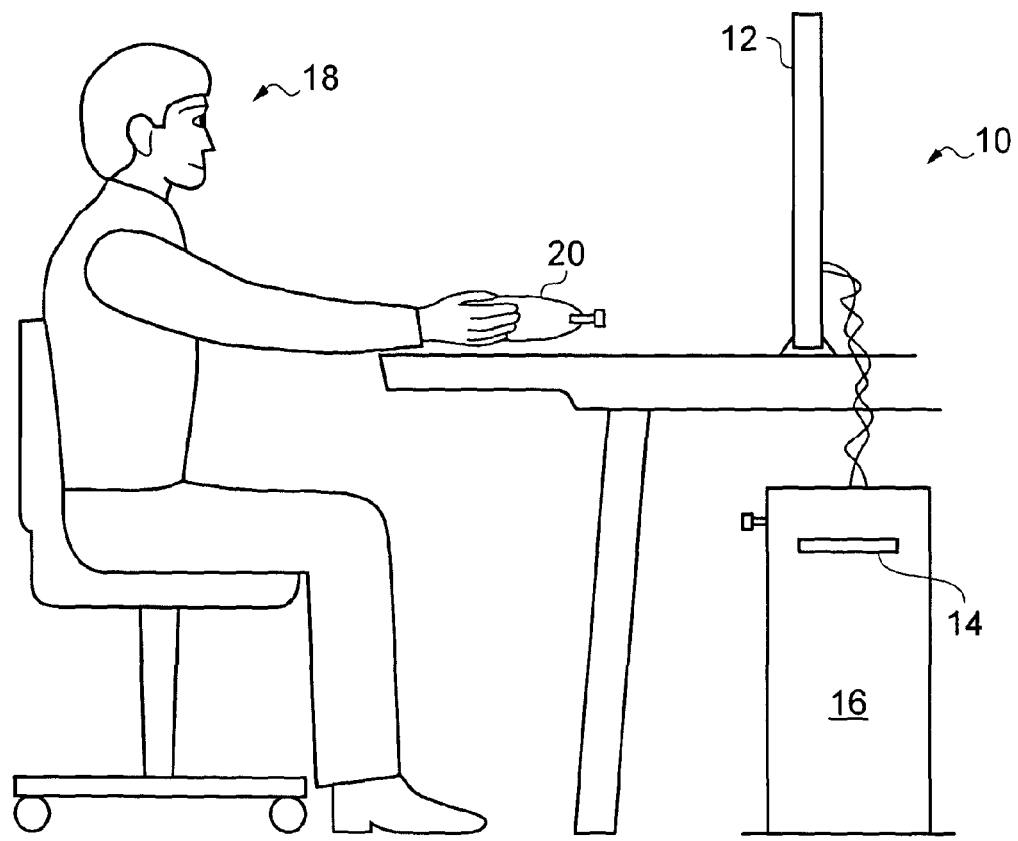
FIG. 2a is an overall view of one embodiment of an apparatus for determining an optimum colour combination of an image on a background that is different colour to the image.
FIG. 2b is an overall view of an alternative embodiment of a system for determining an optimum colour combination of an image on a background image which operates in conjunction with a remote database.

FIG. 2 is an overall view of an embodiment of an apparatus 10 for determining an optimum colour combination of an image on a background. The apparatus 10 comprises a display 12 operating under control of a microprocessor 14 that is typically housed in a personal computer (PC) 16 which is operating under control of software.

Figure 6:
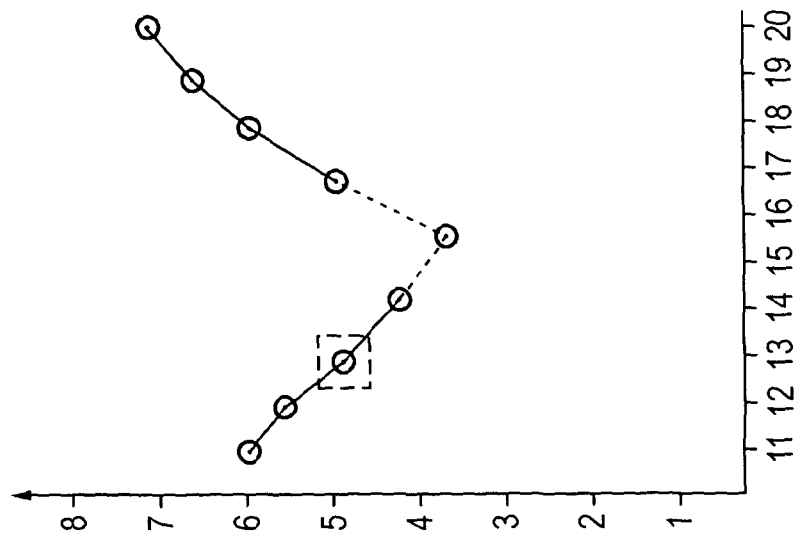
FIG. 6 is a diagrammatical view of a display that shows one example of a user selectable menu.

Apparatus 10 detects, measures and assesses operator fatigue and includes a means for presenting an image to be viewed, by a subject 18, such as display 12. The subject 18 interacts with a user-machine-interface (UMI), such as a mouse 20 and activates a timer when registration of stereoscopic images 80 and 90 (FIG. 6) are perceived by right and left eyes 2 and 4, so as to provide a reaction time.

A means for storing the reaction time (T1) is provided in the PC 16 and a means is provided for varying 70 the image(s) to be viewed 80 and 90 for a second time interval. For example the intensity of red (R), green (G) and blue (B) primary colour signals of display 12 may be varied in a stepwise manner and as shown in the colour chart in FIG. 7

When this procedure is completed a second reaction time (T2) is obtained. Times T1 and T2 are stored in the memory means in PC 16 and times are shown on the table in FIG. 3b. Individual settings for the R, G and B signals are shown on FIG. 3a for attempts 1 to 10 inclusive.

These procedures are repeated for setting for specific colour settings, and by varying one of the colours. In the example shown in FIGS. 3a and 3b, the settings of the red and blue colour settings remain constant and fixed and the green colour setting is varied in a predictable manner.

Figure 3C:
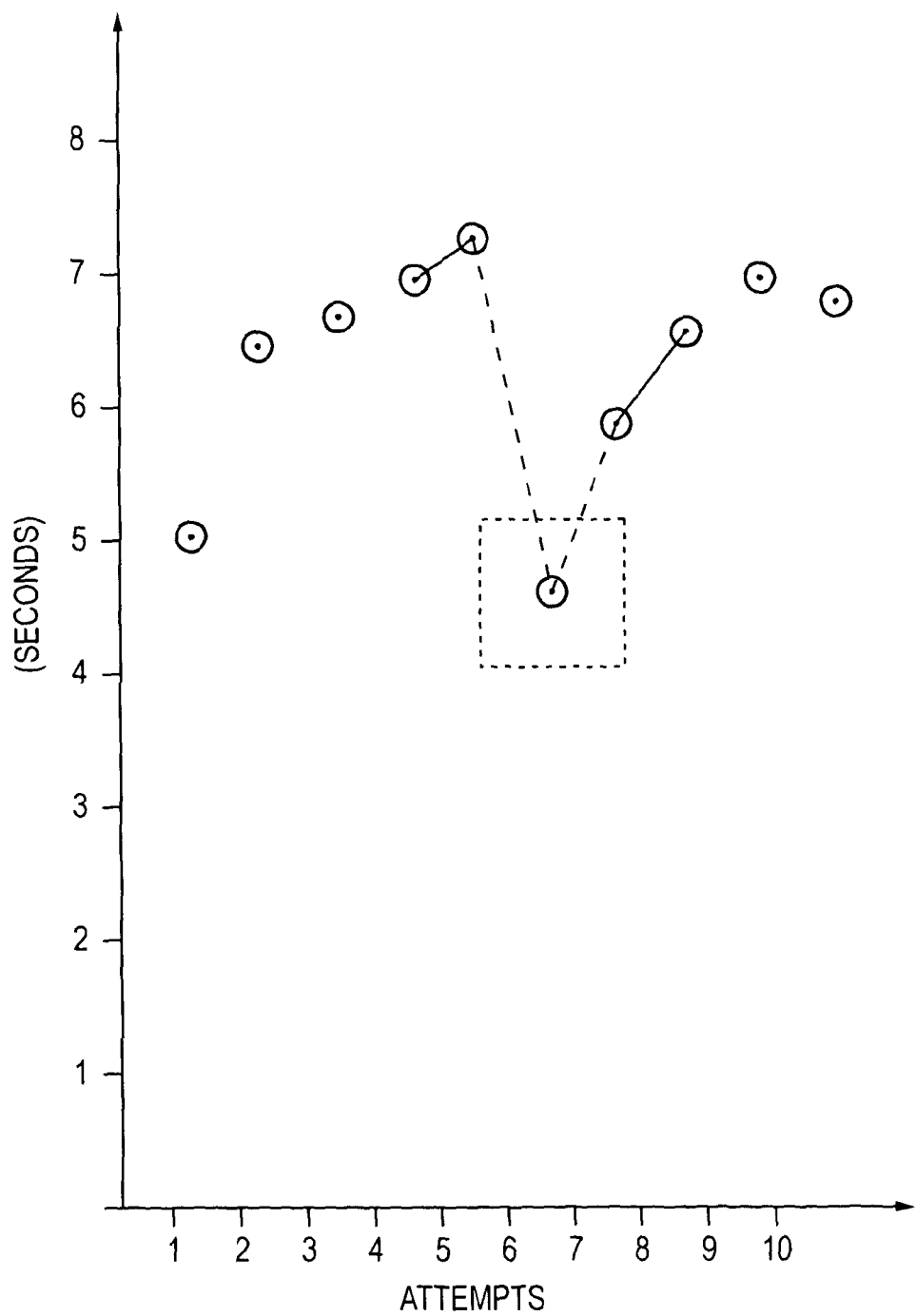
FIG. 3c is a graph plotting reaction times corresponding to the attempts recorded in FIGS. 3a and 3b.

Results for the attempts 1 to 10 are stored and may be analysed for a 'best fit' curve, as well as being plotted on the graph shown at FIG. 3c and this part of the fatigue detecting, measuring and assessing process is referred to as the macro tuning stage.

The reason for the macro tuning stage is that relatively large stepwise variations of colours can be achieved. In the particular example shown and described with reference to FIGS. 3a to 3c, the optimum macro signal readings are at attempt number 6—that is the combination of colour signals that provides the shortest reaction time of 4.9 seconds—and the colour settings are: 255 (R), 150 (G) and 255 (B). The optimum time is shown as a minimum on the graph at FIG. 3c and is seen clearly as a minimum, highlighted inside the dotted box.

Reference is now made to FIGS. 9a to 9d which indicate how combinations of colour are combined in order to arrive at a third colour combination which is more comfortable for a user and so enables a user to register and read images more accurately and more quickly with less stress imposed on the eye.

Figure 4C:
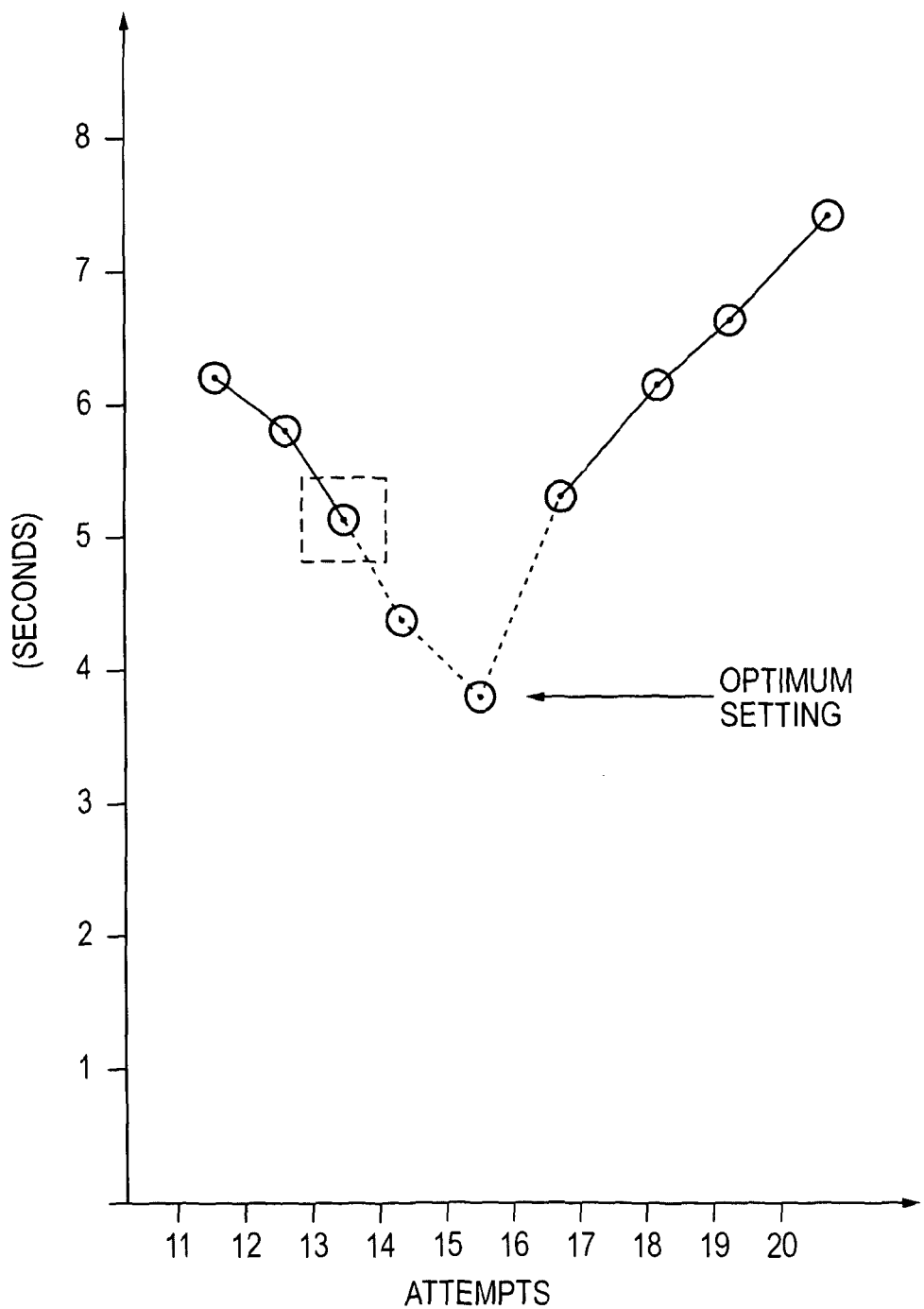
FIG. 4c is a graph plotting reaction times corresponding to the attempts recorded in FIGS. 4a and 4b.

The process is to a large extent repeated but for smaller variations in colours and this is shown in FIGS. 4a to 4c. This process, which is also referred to as fine tuning taking place from the data derived in the macroscopic tuning stage, described above and shown as sample #6 and depicted on FIG. 3c in a square dotted box around the point 4.9 seconds.

The values (R:255, G:150 and B:255) shown at sample #6 in the table at FIG. 3b, are then taken as a start values for the fine tuning stage. The dotted box, corresponding to sample 6 appears as sample #13 in the table shown in FIG. 4b that shows results obtained during the fine tuning stage. Relatively smaller variations of the colour combinations are then made and this fine tuning is illustrated in the table shown in FIG. 4b. The manner in which this is achieved is described below with reference to FIGS. 6 to 8.

The results of the fine tuning are plotted and shown on the graph in FIG. 4c. A clear optimum setting is seen at sample #15, corresponding to the colour combination R:150, G: 170 and B:255. The user 18 or a remote operator (not shown) then is provided with the option—ideally from a pre-selectable menu—to configure display settings to suit his/her optimum combination of colours.

Algorithms are provided in the personal computer (PC) 16 for deriving an optimum colour corresponding to the quickest reaction time. Details of an example of an algorithm are given below with reference to FIGS. 8a to 8e. An automatic display setting may then be chosen and this is optionally stored as part of a user's a personal profile. Alternatively results and records may be displayed, transmitted to a remote recipient, stored on a database or held as part of a user's profile for automatic installation at switch on or log on.

Optionally a user may store their preferred display screen settings on a mobile device, such as a portable electronic device, palm held computer, mobile telephone, i-Phone or i-Pad (Registered Trade Mark), laptop computer or dongle, so that, when encountering an unfamiliar display, a signal can be transmitted to the display (optionally via the Internet, or an intranet network, or directly using Bluetooth (Trade Mark) or infra red signal). This may be especially useful for temporary workers, who may have to work at new workstations especially from a point of view of time that is spent on training and induction of new employees.

One way in which this may be facilitated is to indicate that a particular display or screen is compliant or is capable of automatically resetting its colour signals (chrominance, brightness and contrast settings); is for a logo or icon to be presented, on a desktop or homepage of a display, thereby indicating to users that they may use their own personal display settings to configure a display for either temporary use.

Figure 5:
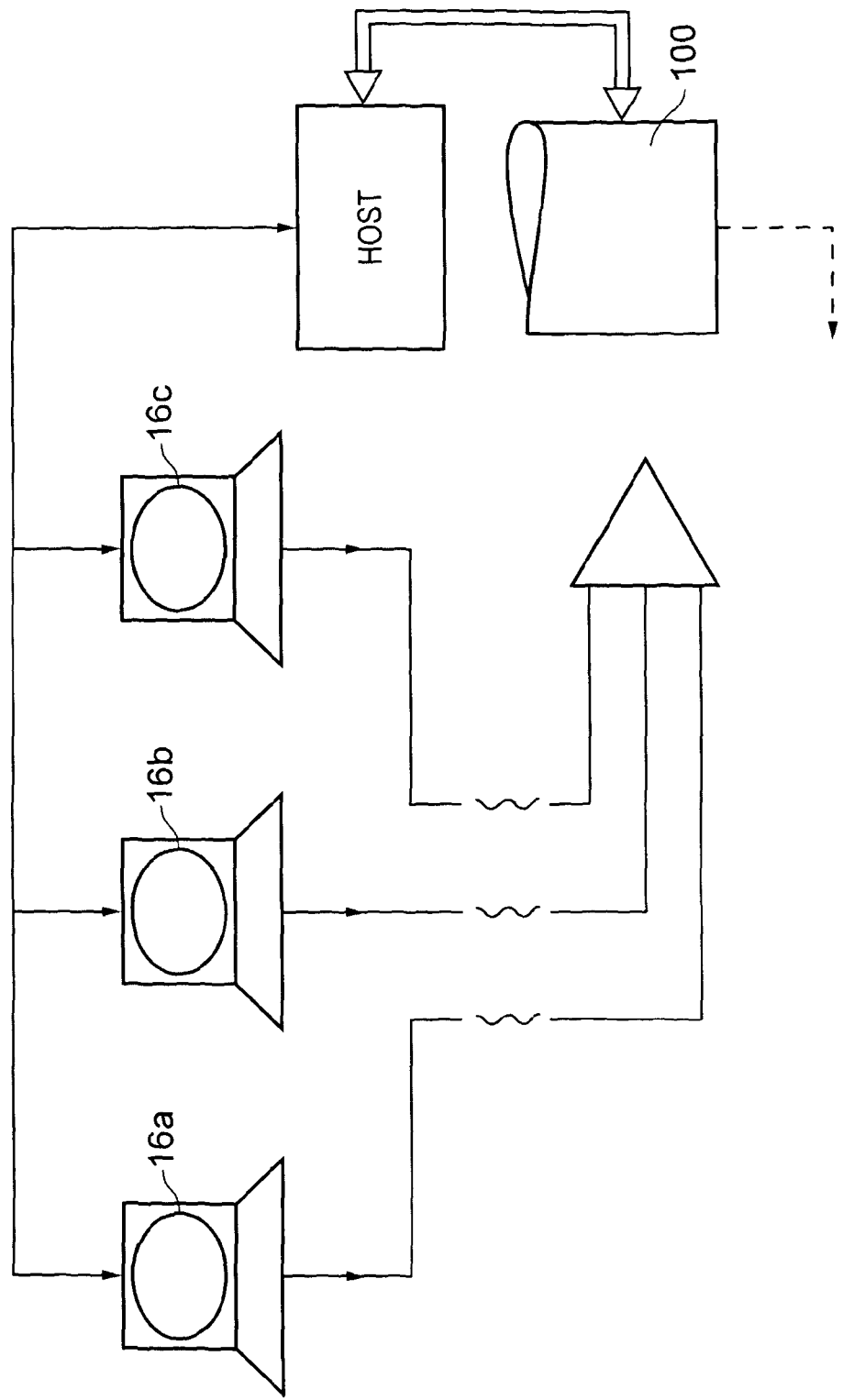
FIG. 5 is an example of a network of individual displays at separate work stations interconnected and in communication with a host station remote database.

Variation may be made by connecting individual systems together in the form of a network or via the Internet and storing records on a database. An example of such a system is shown in FIG. 5, which depicts advantage of this is that records of a number of personnel can be compared, for example in a large organisation. Optionally the host is configured to function as a control station and is able to monitor and manage individual work stations.

In addition other forms of data can be captured and stored and these include: details of a person's identity, how long a person is at a work station, time periods of active work—for example is the user more active in the morning or in the evening. Activity of a user may be monitored automatically by keystrokes or other activity/presence detecting software. Such data may be useful in determining when a user is experiencing fatigue or eyestrain.

In another embodiment image control, monitoring and assessment software may be downloaded from a remote location, such as a secure database. This software may be provided to one or a plurality of users, substantially at the same time. The provision of a database enables storage of data from a variety of users to be made and a comparison of relative performance so that any marked decline in performance can be quickly identified and remedial action taken if appropriate.

Alternatively, or in addition to the above, data can be embedded in software or operating systems so as to provide a user with an option of pre-setting screen parameters when installing a new piece of software.

Figure 7:
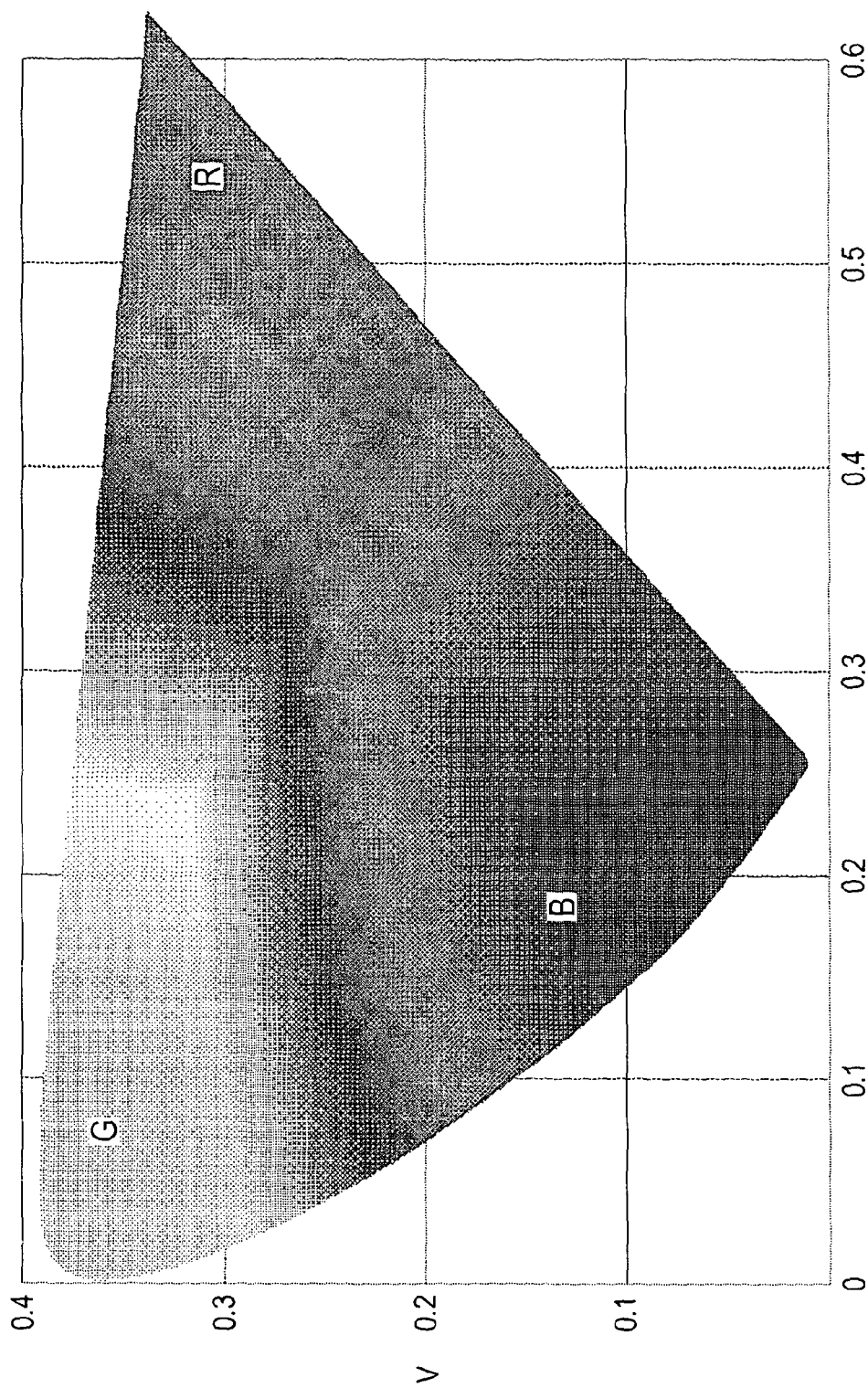
FIG. 7 is one example of a colour chart (as described at http://en.wikipedia.org/wiki/File:CIE_1960_UCS.png) and indicates one way in which a spectrum of colours may be represented on a two dimensional surface.

Referring now to FIGS. 7 to 9, in which FIG. 7 shows a colour chart and indicates one way in which colours are represented on a two dimensional surface. There are many alternative colour charts that are used in display screen design and in communicating concepts of colour to artists, designers and users of displays. The variation can be achieved by a combination of changing the hue and chrominance.

FIG. 8 is an extract from a hexadecimal table, for example as shown at http://www.december.com/html/spec/color-shades.html; and, whilst only depicted as grey scales for the purpose of the present application, access to the website indicates to a user that a myriad colour combinations are achievable by varying controllers and intensity of colour sources, whether these are originating from a liquid crystal display, a cathode ray screen, a plasma display or any other image projecting device.

Reference is now made to FIGS. 9a-9d, which illustrate graphically steps in one example of an iterative technique and show how third and subsequent colour combinations are selected, and the relationship between reaction times and subsequent selection of colour combinations.

Figure 9A:
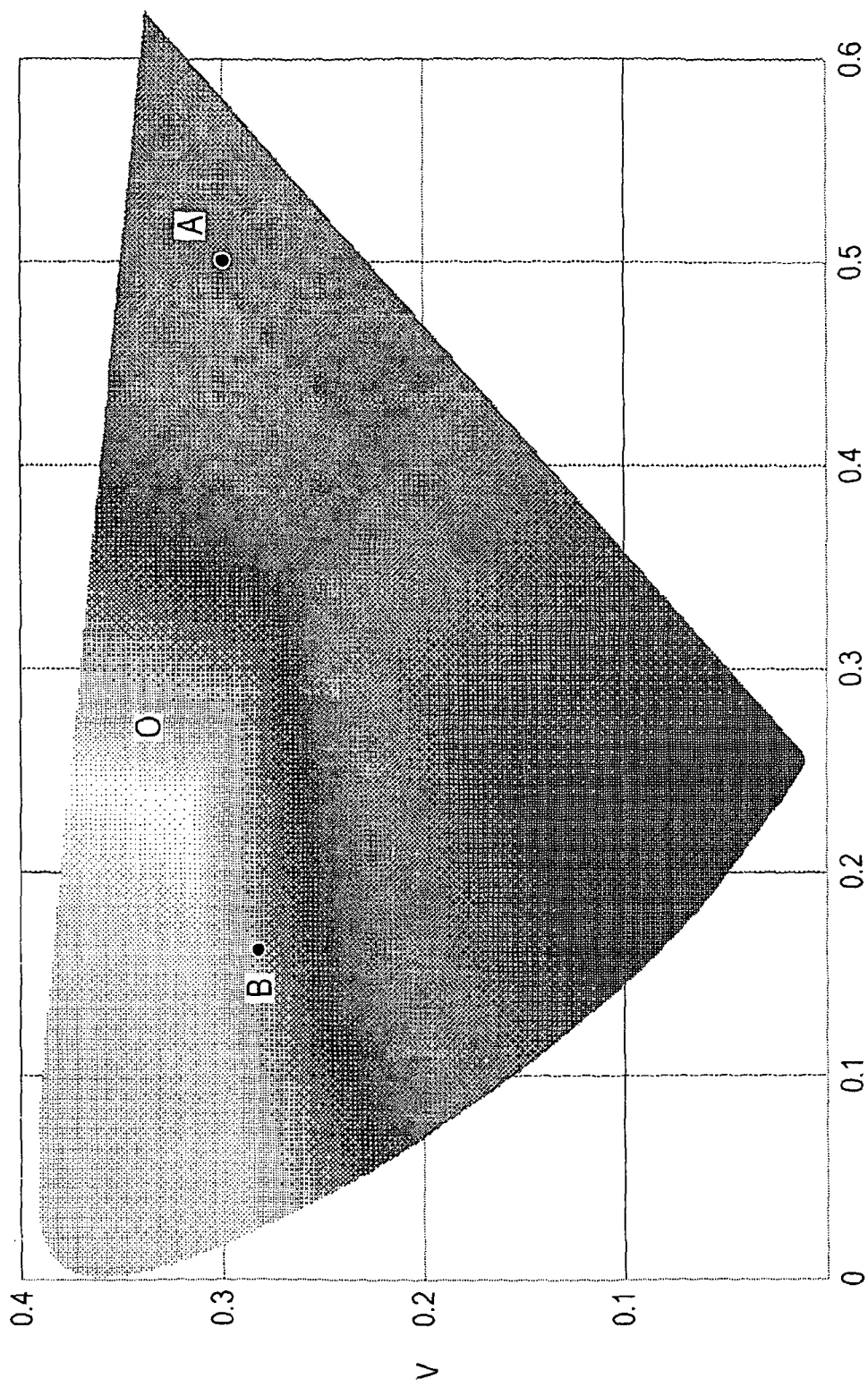
FIGS. 9a-9d are annotated versions of FIG. 7 and depict steps, according to one example of an iterative technique, using extrapolation, and show how a third (and subsequent) colour combination is selected.

FIG. 9a shows graphically the first colour combination, of an image and a display screen colour. This first colour combination may be selected by a user or can be provided automatically under control of software. For the purposes of this example the image is black. Variation to this combination may be used, but for the sake of clarity the colour of the image (text) is kept constant throughout this example. The colour of the display background that corresponds to the first colour combination is show as point A on the colour chart 9a, which is at the red end of the spectrum. The colour of the display background that corresponds to the second colour combination is show as point B, which is towards the green region on the colour chart 9a. It is noted that the region of balanced white light O is at the origin of three axes.

Figure 9B:
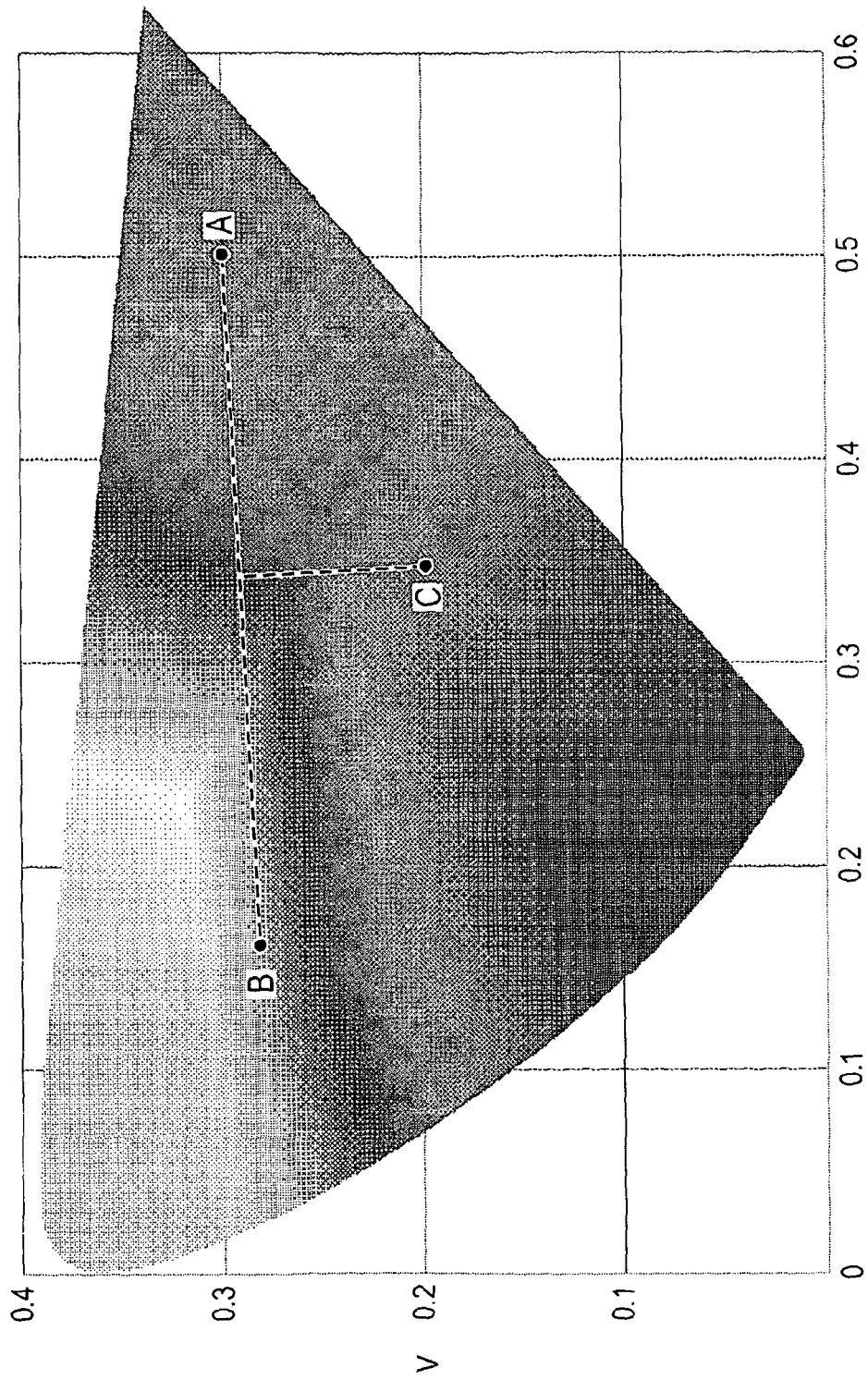

Referring to FIG. 9b an interpolation technique is used to derive point C, which corresponds to a third background colour. Once this third background colour is obtained, the user is presented with a new image and the timer is restarted.

Figure 9C:
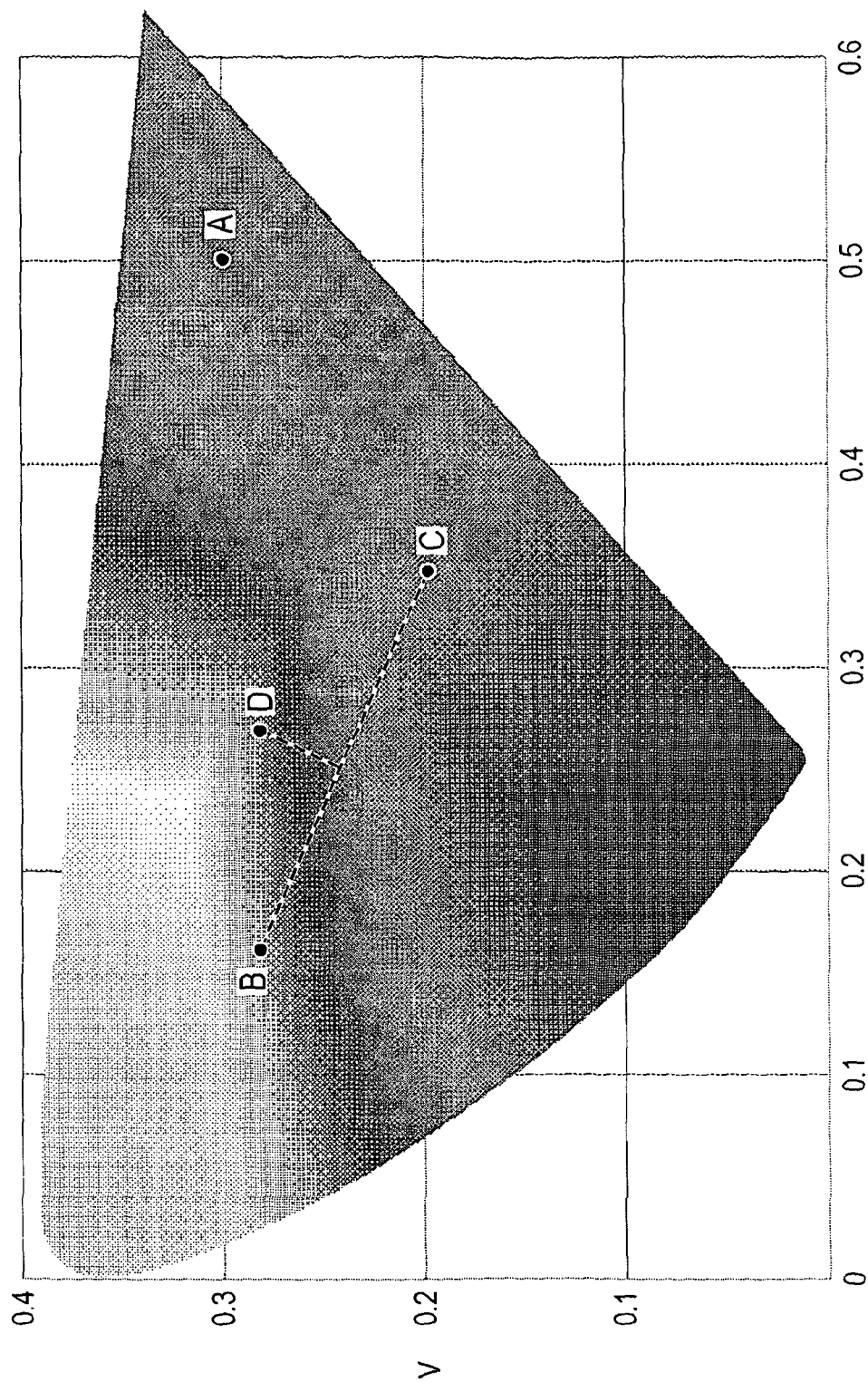
Figure 9D:
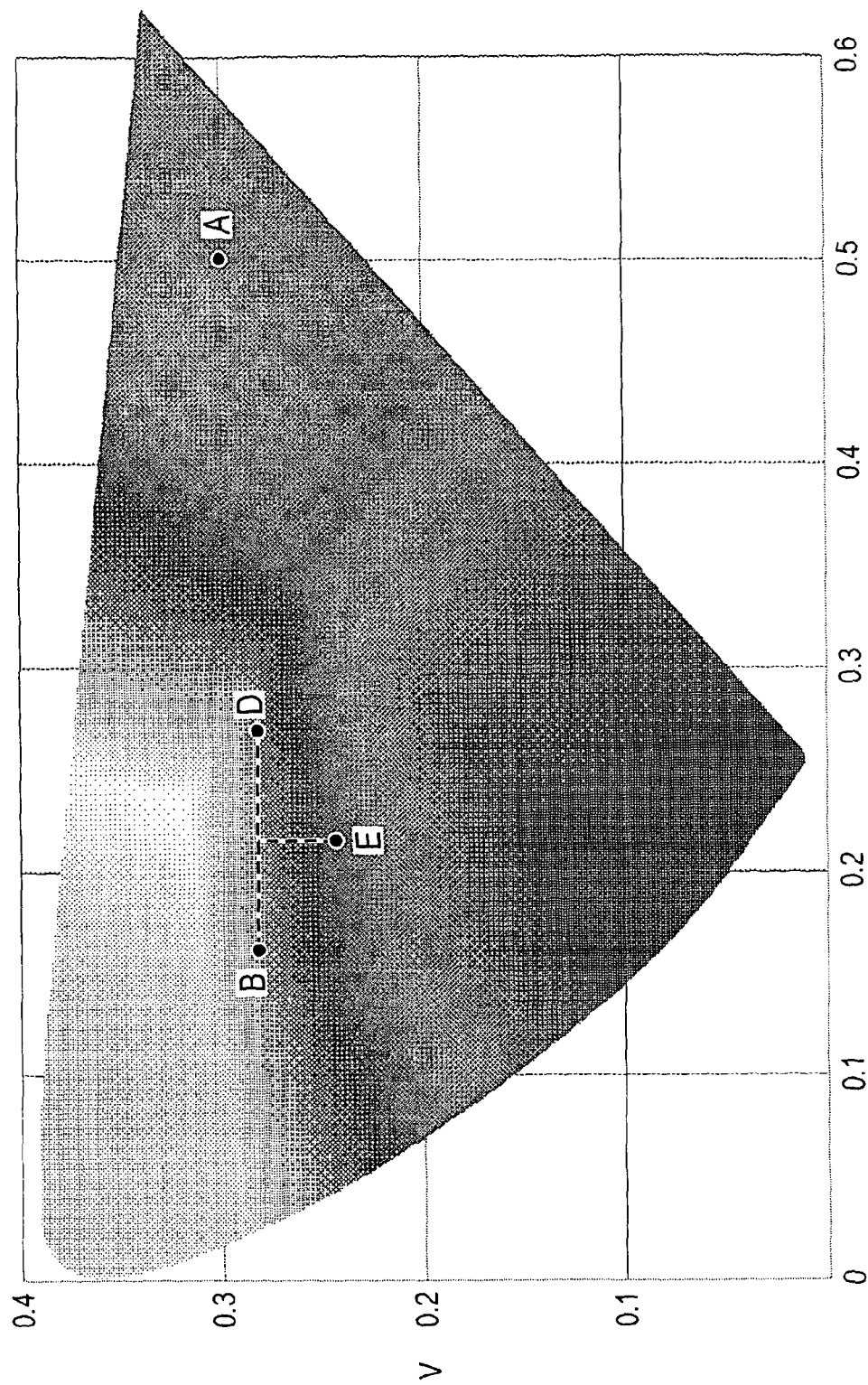

The resultant reaction time for background colours B and C are lower than for A, consequently, these two points are used to derive a fourth point D, shown on FIG. 9c. Point D corresponds to a new background colour and this is then used to present the next background colour and the trial is repeated, using the two shortest time periods in order to derive the next point E, which is shown on FIG. 9d.

It is to be appreciated that the examples described and that the Figures are for illustration purposes only and other configurations are possible. For example variation to the invention may be made in that control software for performing a fatigue assessment method may be supplied in a machine readable form, ideally recorded on a data medium for use with a computer. Alternatively the software may be transmitted from a remote location or accessed via the Internet.

Optionally data may be encrypted or supplied in a once use format or with a limited number of prescribed uses.

One such modification is to provide a user with a pre-set code or tab key or combination of keys, so as to enable the user to switch off a pre-set colour combination, as required, and to return to normal spectral balance.

Another feature is to provide an automatic colour variation, in contrast hue or brightness, so that night-workers are provided with an artificial advancing effect of daylight. This can be achieved for example by introducing, at certain times, a slight yellow or red hue to a display. Alternatively this can be achieved by filtering certain wavelengths.

It is also understood that the invention may be used to reduce screen fatigue and/or the symptoms associated with Computer Vision Syndrome (CVS) in order to improve a user's experience, accessibility and operator performance and/or productivity.

The invention has been described by way of several embodiments, with modifications and alternatives, but having read and understood this description further embodiments, and modifications, will be apparent to those skilled in the art.

All such embodiments and modifications are intended to fall within the scope of the present invention as defined in the accompanying claims.

The invention claimed is:

1. A method of determining an optimum colour combination of text on a background that is of a different colour to the text and applying that colour combination to a display so as to reduce eye strain, the method comprising:
   selecting, a first colour combination of text and background to be presented to a subject;
   initiating a timer when the first colour combination is presented to the subject so that in use, time taken by the subject to read the text in the first colour combination with right and left eyes is recorded, thereby providing a first reaction time corresponding to the first colour combination;
   storing the first reaction time in a memory;
   selecting a second colour combination of the text and background to be presented to the subject;
   initiating a timer at a start of a second time interval, so that a second reaction time is recorded when the subject has read the text displayed in the second colour combination, thereby providing a second reaction time which is stored in the memory;
   deriving a third colour combination of text and background in accordance based in part upon an interpolation using points A and B on a colour chart, where points A and B represent the first background colour and the second background colour, respectively and are used to derive a point C which corresponds to a third background colour;
   presenting the derived third colour combination to the subject and initiating a timer so that a third reaction time is recorded when the subject has read the text displayed in the third colour combination;
   (a) comparing the first reaction time, the second reaction time, and the third reaction time using a comparator;
   (b) selecting the two shortest duration reaction times;
   (c) deriving a fourth colour combination of text and background colour based in part on interpolation using background colours corresponding to the two shortest duration reaction times;
   repeating steps (a) to (c) until an optimum colour combination for the subject is achieved;
   storing the optimum colour combination in the memory; and
   providing the optimum colour combination of text and background to a display on demand.

2. A method according to claim 1, further comprising:
   varying at least one of the first colour combination, the second colour combination, the third colour combination and the fourth colour combination, by decreasing intensity of a primary colour.

3. A method according to claim 1, further comprising:
   deriving a different colour combination using a polynomial interpolation technique.

4. A method according to claim 1, further comprising:
   varying a contrast of the text and display background automatically.

5. A method according to claim 1, wherein:
   the text comprises words which are meaningless and consist of randomly arranged letters.

6. A processing system including a plurality of displays and a database and is operable to operate the plurality of displays to provide an optimum colour combination of text on a background, that is of a different colour to the text, to a user on demand, the system comprising:
   a selection means presents a first colour combination of text and background, a timer is initiated when the first colour combination to be presented to the user so that, in use, the time taken by the user to read the text in the first colour combination with right and left eyes is stored in a memory as a first reaction time corresponding to the first colour combination;
   the selection means presenting a second colour combination of the text and a background to the user; and the timer is initiated at the start of a second time interval, so that a second reaction time is obtained when the user has read the text displayed in the second colour combination, the second reaction time being stored in the memory;
   means for deriving a subsequent colour combination of text and background based upon an interpolation technique using points A and B on a colour chart, where points A and B represent the first and second background colours respectively and are used to derive point C which corresponds to a third background colour; the means for deriving the subsequent colour combination of text and background presenting a derived third colour combination on the display to the user and the timer is initiated so that a third reaction time is recorded when the user has read the text displayed in the third colour combination;
   the following steps are then performed in order:
   (i) a comparator to compare the first reaction time and the second reaction time with the third reaction time, (ii) selecting the two shortest duration reaction times,
(iii) the means for deriving a subsequent colour combination of text and background colour, based upon the interpolation technique uses background colours corresponding to the two shortest duration reaction times to derive a further colour combination,
repeating steps (i) to (iii) until an optimum colour combination for the user is achieved, and
storing the optimum colour combination in the memory, and
providing the optimum colour combination of text and background to a selected display on demand.

7. A system according to claim 6 that is in data communication with a remote operator.

8. A system according to claim 6, further comprising:
detection means and means to assess user activity so as to provide an indication of risk of operator screen fatigue based upon an assessment of user activity.

9. A system according to claim 8, wherein the means provided to assess user activity comprises:
a headset with goggles or other non-contact monitoring equipment in order to track and/or monitor eye movements.

10. A system according to claim 6, further comprising:
a network of display screens which are adapted to display a user preferred colour combination of an image on a background, when a user inputs their user identity and/or password and a host station is adapted to assess user activity, for example by monitoring keystrokes, the host station determining when a user is experiencing fatigue or eyestrain.

11. A system according to claim 8, further comprising:
means for detecting a presence of the user.

12. A system according to claim 8, further comprising:
a database to store user records and other data.

13. A system according to claim 8, further comprising:
a comparator to compare relative performance of a user at different time periods.

14. A system according to claim 8, further comprising:
an alerter to provide an alert signal or alarm alerting the user to symptoms of fatigue.

15. A display for use with the system of claim 8, further comprises:
means for storing a particular selection of one or more colour signals;
means for selecting a specific colour combination; and
means to input a user identity.

16. A system according to claim 8, wherein stored data includes data from the group comprising:
details of a user's identity;
how long a user has been at a work station; and
time periods of active work.

17. A system according to claim 16, further comprising:
means for using data to determine a decline in performance, so as to detect when a user is experiencing fatigue or eyestrain.

* * * * *